United States Patent [19]
Wallrafen

[11] Patent Number: 5,140,233
[45] Date of Patent: Aug. 18, 1992

[54] CONTROL OF WINDSHIELD WIPER BY INTEGRATION AND DIFFERENTIATION OF SENSOR SIGNAL

[75] Inventor: Werner Wallrafen, Sulzbach, Fed. Rep. of Germany

[73] Assignee: VDO Adolf Schindling AG, Frankfort am Main, Fed. Rep. of Germany

[21] Appl. No.: 621,042

[22] Filed: Nov. 30, 1990

[30] Foreign Application Priority Data

Jan. 12, 1990 [DE] Fed. Rep. of Germany ....... 4000736

[51] Int. Cl.$^5$ ................................................. B60S 1/00
[52] U.S. Cl. ...................................... 318/264; 318/483;
    318/DIG. 2; 15/250.17; 15/DIG. 15
[58] Field of Search ................ 318/443, 444, DIG. 2, 318/483, 643; 15/250 C, 250.12, 250.13; 307/10.1

[56] References Cited

U.S. PATENT DOCUMENTS

| | | | |
|---|---|---|---|
| 4,131,834 | 12/1978 | Blaszkowski | 318/483 |
| 4,542,325 | 9/1985 | Kobayashi et al. | 318/483 |
| 4,636,643 | 1/1987 | Nakamura et al. | |
| 4,703,237 | 10/1987 | Hochstein | |
| 4,710,878 | 12/1987 | Iyoda | 318/444 X |
| 4,740,735 | 4/1988 | Hayashi | |
| 4,827,198 | 5/1989 | Mueller et al. | 318/483 |
| 4,916,374 | 4/1990 | Schierbeek et al. | 318/483 |
| 4,987,354 | 1/1991 | Steinmann | 318/444 |
| 5,017,847 | 5/1991 | Leistenschneider | 318/DIG. 2 |

FOREIGN PATENT DOCUMENTS

| | | |
|---|---|---|
| 0102622 | 8/1983 | European Pat. Off. . |
| 0333564 | 10/1989 | European Pat. Off. . |
| 2630470 | 12/1978 | Fed. Rep. of Germany . |
| 3314770 | 4/1983 | Fed. Rep. of Germany . |
| 3538553 | 7/1987 | Fed. Rep. of Germany . |

Primary Examiner—A. Jonathan Wysocki
Attorney, Agent, or Firm—Martin A. Farber

[57] ABSTRACT

A method and a system for controlling a windshield wiper, particularly on a motor vehicle, provides that the windshield wiper is automatically activated as a function of the intensity of rain. A frequency-limited variation of the signal of a sensor serves as a measure of the intensity of the rain.

10 Claims, 3 Drawing Sheets

CONTROL OF WINDSHIELD WIPER BY INTEGRATION AND DIFFERENTIATION OF SENSOR SIGNAL

FIELD AND BACKGROUND OF THE INVENTION

The present invention relates to a method and a system for controlling a windshield wiper, particularly on a motor vehicle, wherein the windshield wiper is automatically turned on as a function of the intensity of the rain.

Devices for controlling windshield wipers are known in which the windshield-wiper motor automatically starts when a predetermined threshold of wetting of the windshield by rain is exceeded. Various sensors are known for detecting the wetting of the windshield, but with them various disturbing influences such as, for instance, dependencies on temperature, long-term drifts, manufacturing tolerances and vehicle-specific differences lead to errors.

SUMMARY OF THE INVENTION

It is an object of the present invention to permit control of a windshield wiper as a function of the intensity of the rain without error introduced the above-indicated disturbing influences.

According to the invention, a frequency-limited variation of the signal of a sensor serves as measure of the intensity of the rain.

In this connection, it can either be provided that the signal is conducted over a band-pass filter and that the effective value of the band-limited signal is formed, or it can be provided that an average value of the signal is formed and the variance or standard deviation of the instantaneous signal from the average value is calculated.

The invention is based on the fact that continuous movements of water drops produce stochastic signals which are entirely absent in the case of dryness.

In accordance with a further development of the invention, a measure of the accumulated rain is obtained in the manner that the value of the instantaneous variation is integrated, and the windshield wiper is connected when the integrated amount exceeds a threshold value.

In this connection, it may be provided preferably that the integration is restarted after each wiping process.

Another further aspect of the invention is that, after the integration, differentiation with large time constant is effected in order to compensate for evaporation of water.

Furthermore, in accordance with another further feature, erroneous results by stochastic signals which are produced in the absence of water drops is avoided because only values of the variation which exceed a threshold value are evaluated and integrated.

In a further development of the invention, it is provided that a variation which is less than a predetermined threshold value is detected as a dry windshield, and that the sensor signal present at this time serves as comparison value for subsequent triggering criteria. In this case the windshield wiper is preferably connected when the sensor signal exceeds the comparison value.

According to the invention, there is provided an advantageous arrangement for the carrying out of the method in which the sensor is connected via an analog/-digital converter (4) to a microcomputer (5), and that a program in accordance with the method of the invention is provided for the microcomputer (5). In this case, the sensor is preferably a capacitive wetness sensor (1).

BRIEF DESCRIPTION OF THE DRAWINGS

With the above and other advantages in view, the present invention will become more clearly understood in connection with the detailed description of a preferred embodiment, when considered with the accompanying drawing, of which.

DETAILED DESCRIPTION OF THE PREFERRED EMBODIMENT

Figure 1:
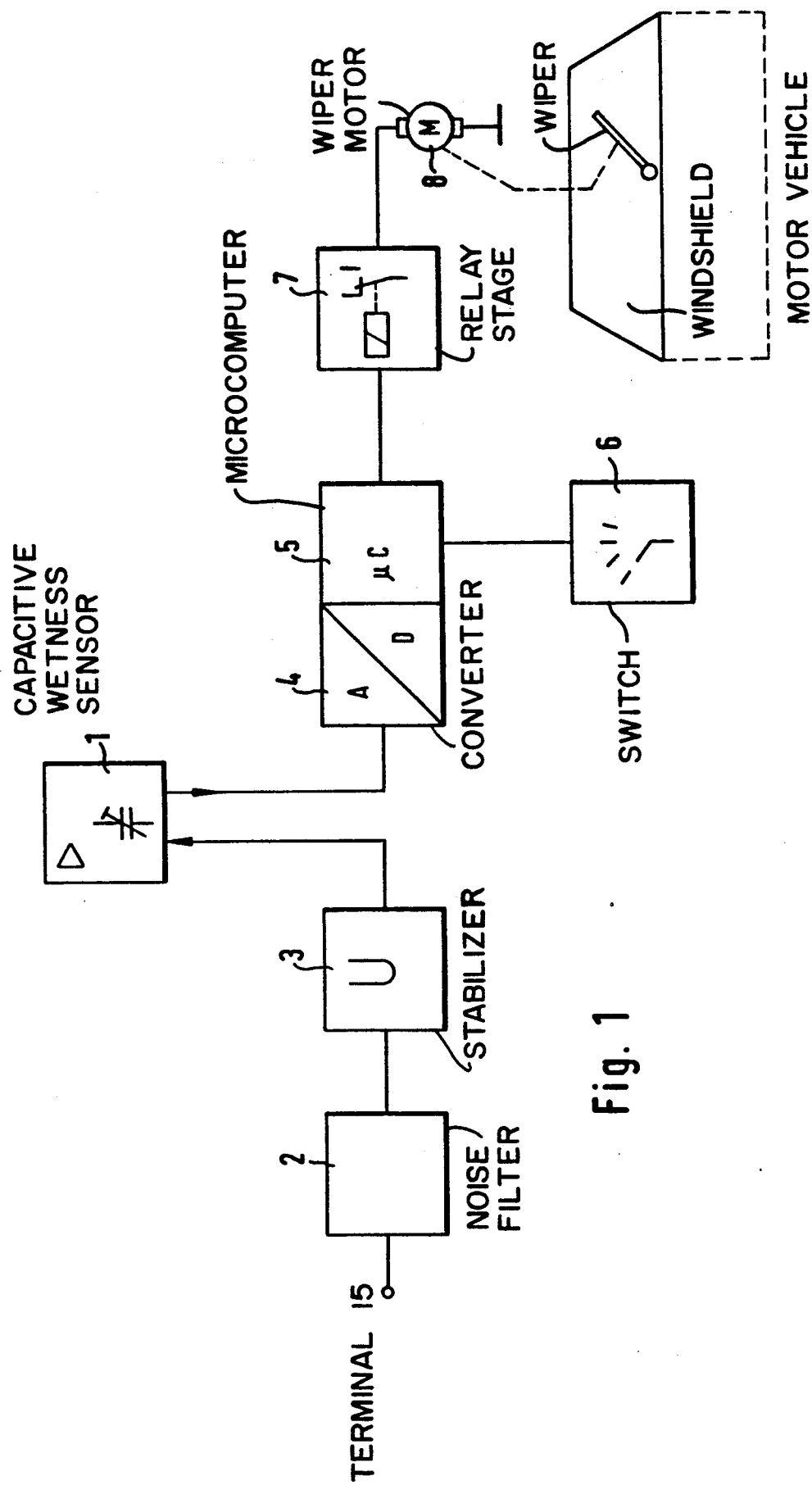
FIG. 1 is a block diagram of an arrangement for the carrying out of the method of the invention.

In the device shown in FIG. 1, the degree of wetting of the windshield is determined by means of a capacitive sensor 1 to which operating voltage is fed via the terminal 15 of the car electrical system via a noise-voltage filter 2 and a stabilization circuit 3. Capacitive wetness sensors are known per se and need not be explained in detail for an understanding of the present invention. An amplifier (not shown) is included with the sensor 1 so that the output voltage of the sensor is fed directly to an analog/digital converter 4 of a so-called single-chip microcomputer 5. The microcomputer 5 is connected to an operating switch 6 which is preferably developed as a steering-column switch, and has detent positions for continuous operation and automatic operation as well as a touch position for a single wipe. The motor 8 of a windshield wiper is connected via a relay stage 7 to an output of the microcomputer 5.

Figure 2:
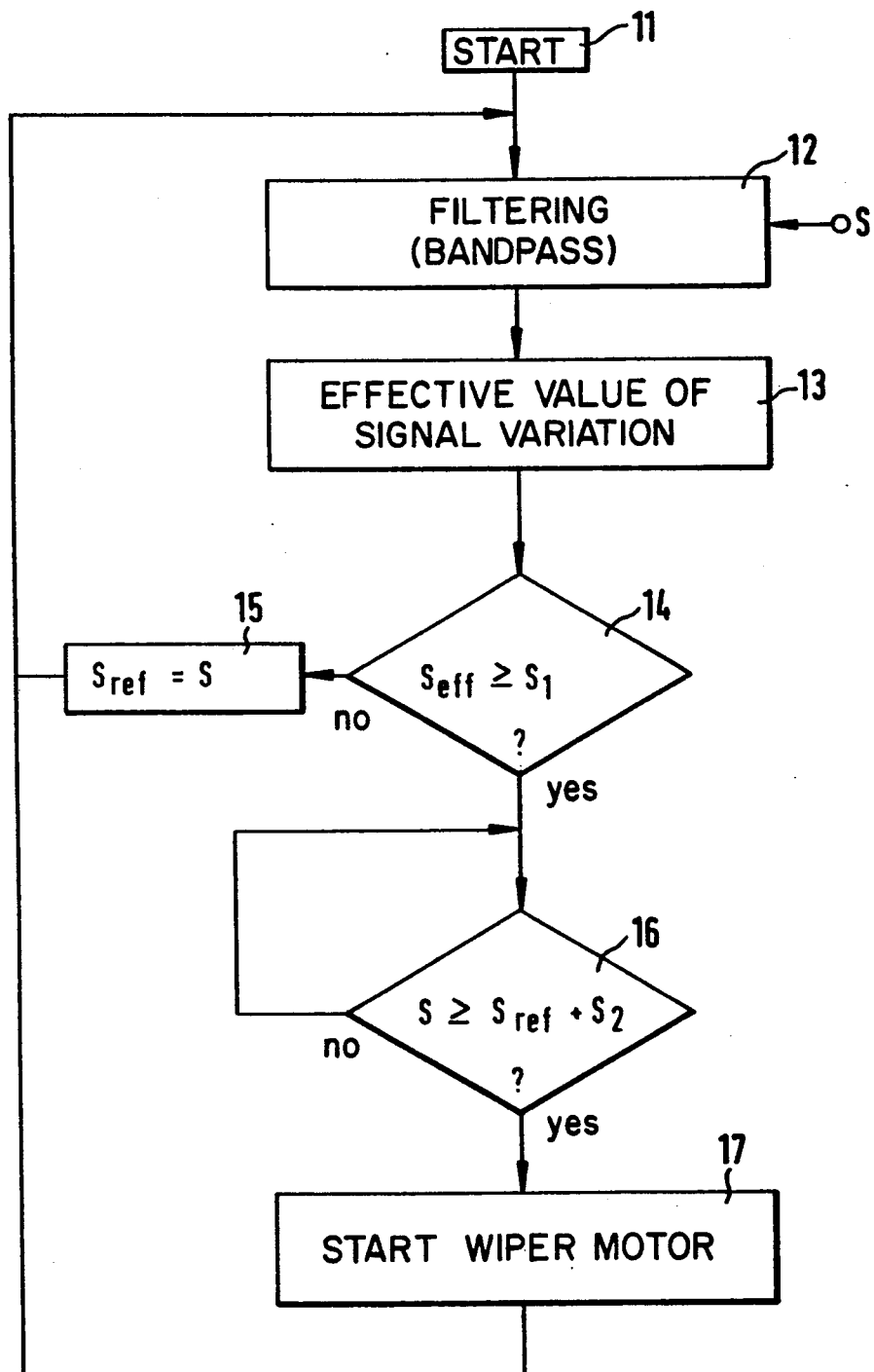
FIG. 2 is a flowchart of a program intended for the microcomputer in the arrangement according to FIG. 1.

In the program shown in FIG. 2, a comparison value for the sensor signal is first of all established by evaluation of the variation of the sensor signal S whereupon a signal for the starting of the wiper motor is produced by comparison of the actual sensor signal with the comparison value. For this purpose, after the starting of the program at 11 in the program part 12, a value is read in for S and subjected to band-pass filtering together with previous signal values. The variation of the filtered signal is then determined at 13. The variation can, for instance, be the effective value. The value $S_{eff}$ thus obtained is compared with a first threshold value $S_1$. This threshold value is somewhat larger than the stochastic variations (noise) which are present in the sensor signal if the windshield is dry.

If the value $S_{eff}$ exceeds the first threshold value $S_1$ this is a clear indication that rain is present. After the branching 14, a comparison value $S_{ref}$ which is to be stored is set equal in the program part 15 to the actual statistical sensor signal S. This comparison value $S_{ref}$ unambiguously characterizes the static sensor signal S when the windshield is dry. Thereupon, starting with the filtering 12, the program described above is repeated until, upon the occurrence of rain, the effective value $S_{eff}$ exceeds the threshold value $S_1$. It is then tested at 16 whether the actual sensor signal S is greater than or equal to the stored comparison value $S_{ref}$ plus a second threshold value $S_2$. It is thus determined, independently of the aforementioned disturbing variables, that rain is present so that the windshield wiper can be started at 17.

In the method of the invention, the windshield wiper can in itself be turned off in various manners. It may advantageously be provided that the windshield wiper in each case carries out one wiping movement and is, in each case, started again by the method of the invention. In the event of stronger rain, this results in a continuous wiping movement since a signal for the starting of the wiper is then possibly produced already during the wiping process.

Instead of the band-pass filtering in the program part 12, a low-pass filtering can also be provided. Band-pass filtering, however, has the advantage that portions of the band of the sensor signal which are of higher frequency and are not caused by the fluctuation of the rain drops are suppressed. These can, for instance, be steep flanks of the sensor signal which are produced when the windshield wiper passes over the sensor.

The advantage of the invention will once again be shown on basis of the following numerical example which is based on practical tests. The sensor signal has, for instance, a value of 1V when the windshield is dry and of 3V when it is wet with rain. Without the method of the invention, a threshold value between these two values would have to be present, for instance, 2V. The above-mentioned influences, such as temperature, aging or dirtying of the windshield, can, however, cause a change of up to 100% in the sensor signal. The variation of the sensor signal is, however, considerably greater when rain is present. The effective value, for example, when the windshield is dry is <2mV and in the case of rain about 20mV. Even if the variation is subjected to the same relative disturbing changes, an unambiguous detection is possible with the aid of a threshold value of, for instance, $S_1 = 5mV$.

Figure 3:
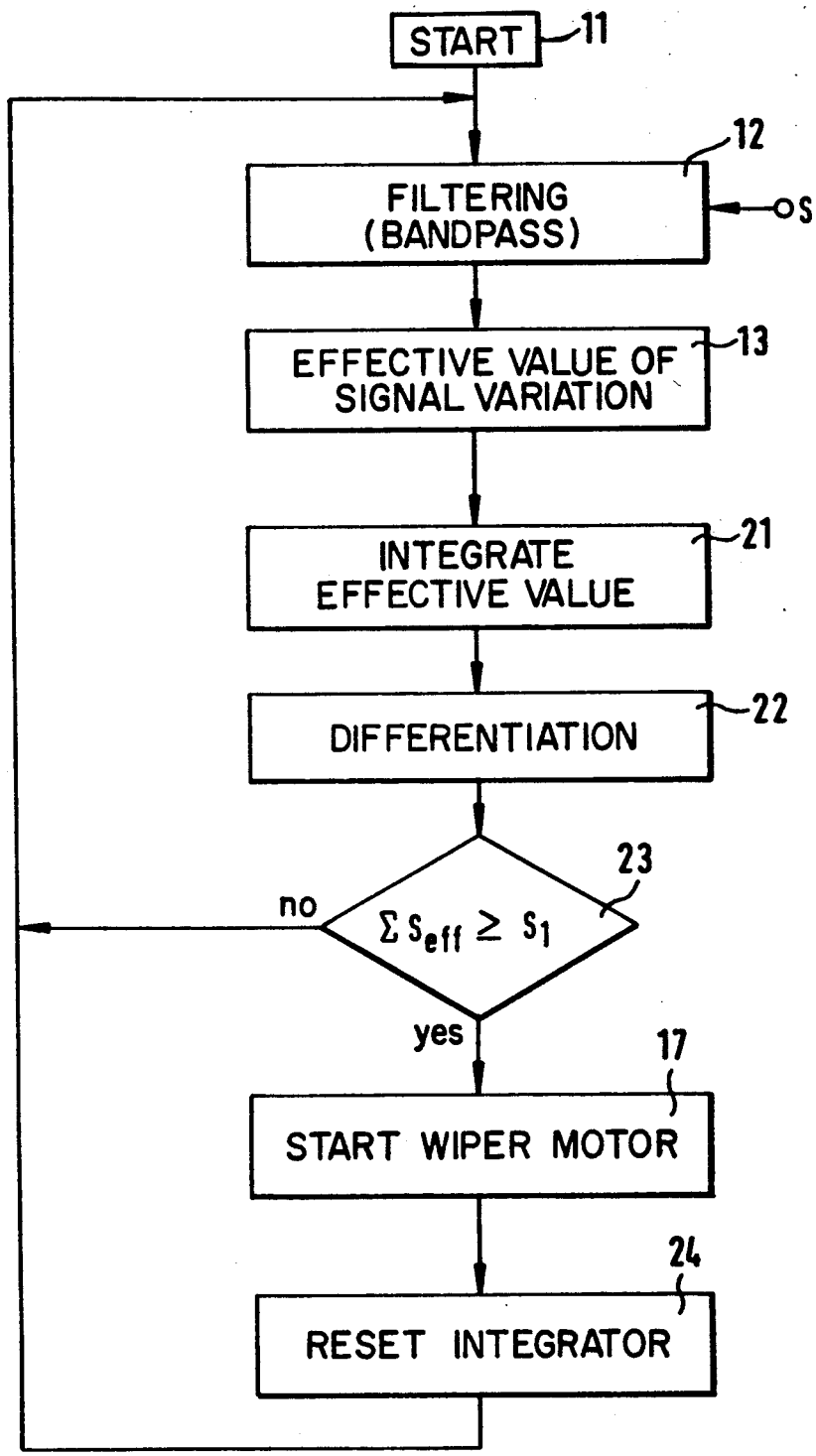
FIG. 3 is another flowchart.

In the program shown in FIG. 3, a filtering is first effected at 12 as in the program shown in FIG. 2 and a determination of the variation in signal effected at 13. The value $S_{eff}$ which is thus determined is integrated at 21, whereby the accumulation of water taking place by the impingement of individual drops of rain on the windshield is practically represented. A differentiation with a large time constant which represents the evaporation of the water is superimposed at 22 on the integration. The differentiation at 22 can be considered also as a high pass filter.

After the completion of program parts 21 and 22, a decision is made at 23 as to whether the integrated and differentiated value $\Sigma S_{eff}$ has already reached a threshold value $S_1$. As long as this is not the case, steps 12, 13, 21 and 22 are repeated. However, if $\Sigma S_{eff} \geq S_1$, then the wiper motor is started at 17. The integrator is then reset at 24 to the initial value, whereupon the program is repeated, starting with the filtering 12.

I claim:

1. A method for controlling a windshield wiper, suitable for a motor vehicle, in which the windshield wiper is automatically turned on as a function of the intensity of the rain, the method comprising the steps of sensing the presence of rain with an electrically activated sensor;

employing a frequency-limited variation of a signal of the sensor to serve as a measure of the rain; and wherein said employing step includes:

integrating the value of the sensor signal;

differentiating a result obtained from the step of integrating, the differentiating being done with a large time constant in order to compensate for the evaporation of water; and activating the windshield wiper when a result of the differentiating step exceeds a threshold value.

2. A method according to claim 1, further comprising the steps, prior to said integrating step, of conducting the sensor signal via a bandpass filter to obtain a band-limited signal; and forming the effective value of the band-limited signal.

3. A method according to claim 1, further comprising the steps, prior to said integrating step, of forming an average value of the sensor signal; and calculating the variance or standard deviation of the instantaneous signal from an average value of the sensor signal.

4. A method according to claim 1, further comprising restarting the integration after each wiping process.

5. A method according to claim 4, further comprising differentiating a result obtained from the step of integrating, the differentiating being done with a large time constant in order to compensate for the evaporation of water.

6. A method according to claim 3, further comprising only values of the variance which exceed a threshold value are evaluated and integrated.

7. A method according to claim 3, wherein a variation which is less than a predetermined threshold value is detected as a dry windshield and that the sensor signal present at this time serves as comparison value for activating the windshield wiper.

8. A method according to claim 7, further comprising activating the windshield wiper when the sensor signal exceeds a comparison value.

9. A system for controlling a windshield wiper, suitable for a motor vehicle, in which the windshield wiper is automatically turned on as a function of the intensity of the rain, comprising an analog-to-digital converter, and a microcomputer; and a rain sensor, the sensor being connected via the analog-to-digital converter to the microcomputer; and the microcomputer is operated in accordance with a program to provide for integration of a signal of the sensor followed by differentiation of a result of the integration to provide said function of the rain intensity.

10. A system according to claim 9, wherein the sensor is a capacitive wetness sensor.

* * * * *